(12) United States Patent
Raviyan et al.

(10) Patent No.: US 9,078,850 B2
(45) Date of Patent: Jul. 14, 2015

(54) SYSTEM AND METHOD FOR EXTRACTING VITAMIN E FROM FATTY ACID DISTILLATES

(75) Inventors: Patcharin Raviyan, Chiang Mai (TH); Kriengkai Soinak, Chiang Mai (TH)

(73) Assignees: The Thailand Research Fund, Bangkok (TH); Chiang Mai University, Chiang Mai (TH); Chumporn Palm Oil Industry Public Company Limited, Chumporn (TH)

( * ) Notice: Subject to any disclaimer, the term of this patent is extended or adjusted under 35 U.S.C. 154(b) by 654 days.

(21) Appl. No.: 13/387,195

(22) PCT Filed: Dec. 23, 2009

(86) PCT No.: PCT/SG2009/000491
§ 371 (c)(1), (2), (4) Date: Jan. 26, 2012

(87) PCT Pub. No.: WO2011/014122
PCT Pub. Date: Feb. 3, 2011

(65) Prior Publication Data
US 2012/0130094 A1    May 24, 2012

(30) Foreign Application Priority Data
Jul. 30, 2009    (TH) .............................. 0901003454

(51) Int. Cl.
  *C07D 311/00*    (2006.01)
  *A61K 31/07*    (2006.01)
  *B01D 9/00*    (2006.01)

(52) U.S. Cl.
  CPC .............. *A61K 31/07* (2013.01); *B01D 9/0013* (2013.01)

(58) Field of Classification Search
  CPC .............................. A61K 31/07; B01D 9/0013
  USPC ......................................................... 549/413
  See application file for complete search history.

(56) References Cited

U.S. PATENT DOCUMENTS

| 5,190,618 | A | 3/1993 | Top et al. |
| 5,670,669 | A | 9/1997 | Hunt |
| 6,838,104 | B2 | 1/2005 | Jacobs |
| 2005/0250953 | A1 | 11/2005 | May et al. |
| 2009/0155434 | A1 | 6/2009 | Brunner et al. |

FOREIGN PATENT DOCUMENTS

FR    2581384    * 11/1986

* cited by examiner

*Primary Examiner* — T. Victor Oh
(74) *Attorney, Agent, or Firm* — Nath, Goldberg & Meyer; Joshua B. Goldberg

(57) ABSTRACT

Various systems and processes for extracting Vitamin E from a fatty acid distillate (FAD) having a Vitamin E component are disclosed. The process includes preparing a mixture of a FAD and a non-polar solvent (e.g., hexane). The mixture can be sequentially cooled to a series of pre-determined temperatures. As the mixture is sequentially cooled to each of the pre-determined temperatures within the series of pre-determined temperatures, non-Vitamin E components present in the FAD can form solid fractions within the mixture at the various pre-determined temperature stages. The process further includes removing the solid fractions from the mixture at each of the pre-determined temperature stages. After completion of a number of cooling and separation stages or cycles, the non-polar solvent can be removed from the remaining mixture to recover a Vitamin E extract.

16 Claims, 2 Drawing Sheets

US 9,078,850 B2

SYSTEM AND METHOD FOR EXTRACTING VITAMIN E FROM FATTY ACID DISTILLATES

This is a National Phase application filed under 35 U.S.C. §371 as a national stage of PCT/SG2009/000491, filed on Dec. 23, 2009, an application claiming the benefit under 35 U.S.C. §119 of Thailand Application No. 0901003454, filed on Jul. 30, 2009, the content of each of which is hereby incorporated by reference in their entirety.

TECHNICAL FIELD

The present disclosure generally relates to the separation or extraction, recovery and refining of Vitamin E from fatty acid distillates. More particularly, the present disclosure describes various embodiments of systems for separating or extracting Vitamin E from such distillates, including a system having a simple and easy to implement design that is capable of processing fatty acid distillates for producing Vitamin E with low energy consumption and short process duration; and corresponding Vitamin E extraction and recovery processes.

BACKGROUND

Studies have shown that Vitamin E exhibits many beneficial properties, such as anti-oxidant and anti-cancer properties, and is able to reduce blood pressure and blood cholesterol, prevent skin ageing and fat oxidation. Due to its numerous health related properties, Vitamin E has been widely used in the manufacture of many health supplements, pharmaceutical products and cosmetics. In addition, Vitamin E is also widely utilized in animal feeds due to its anti-sterility properties. With the increasing demand for Vitamin E supply, there is a pressing need to develop an efficient method, technique or process to provide sufficient Vitamin E to meet the demand of the market.

Currently, Vitamin E available in the market is generally produced via chemical and/or physical processes from natural sources, such as palm oil, soybean oil, avocado, wheat germ and vegetable oils. The currently available methods utilize expensive raw materials and/or catalysts and involve use of complicated separation procedures. In most cases, the yield of Vitamin E from such production procedures is usually unsatisfactory relative to the production cost. Techniques used in the separation of Vitamin E from natural sources also present similar problems and drawbacks. Specifically, as the amount of Vitamin E present in natural sources is relatively low, the separation methods involve a series of complicated procedures, such as enzyme catalysis, transesterification, saponification, and sophisticated laboratory techniques, such as molecular distillation, column chromatography, and supercritical fluid extraction. Hence, the time and cost of production of Vitamin E can be undesirable depending upon production technique.

Given the increasing demand for Vitamin E, a need exists for a Vitamin E production technique that is substantially faster, simpler, cost-effective, and involves lower energy consumption.

SUMMARY

In one aspect of the disclosure, a process for extracting Vitamin E from a fatty acid distillate (FAD) having Vitamin E (e.g., including or carrying a Vitamin E source or component) includes providing a mixture of the FAD and a non-polar solvent; sequentially reducing the temperature of the mixture to a series of pre-determined temperatures; removing solid fractions from the mixture when the temperature of the mixture reaches each of the pre-determined temperatures of the series of pre-determined temperatures; and removing the non-polar solvent from the mixture for recovering Vitamin E from the mixture.

In another aspect of the disclosure, a system for extracting Vitamin E from a FAD having Vitamin E includes a temperature controller for sequentially reducing a temperature of a mixture of FAD and a non-polar solvent to a series of pre-determined temperatures; a separator for separating solid fractions from the mixture when the temperature of the mixture reaches each of a pre-determined temperature within a series of pre-determined temperatures; a removing unit for removing the non-polar solvent from the mixture for recovering Vitamin E from the mixture; and a system control unit coupled to the temperature controller and the separator.

BRIEF DESCRIPTION OF THE DRAWINGS

Embodiments of the present disclosure are described herein with reference to the drawings, in which.

DETAILED DESCRIPTION

Various embodiments of the present disclosure relate to simple and cost-effective techniques, processes or methods for separating or extracting, recovering, and refining Vitamin E from plant-based sources of Vitamin E such as fatty acid distillates (FAD). The present disclosure also relates to structural and functional aspects of a simple Vitamin E extraction system that facilitates melting of FAD; mixing of FAD with a non-polar solvent; reducing the temperature of the FAD and non-polar solvent mixture sequentially across or to a series of pre-determined temperatures; removing solid fractions from the mixture at some or each of the pre-determined temperatures of the series of pre-determined temperatures; and removing the non-polar solvent from the mixture for recovering Vitamin E. As described in detail below, multiple embodiments of a Vitamin E extraction system can include subsystems, devices, and/or structural elements that facilitate or enable the recovery and purification of Vitamin E from FAD using a multiple-stages sequential cooling and separation technique.

Systems, devices, techniques, and processes in accordance with various embodiments of the disclosure enable fast removal of non-Vitamin E components from FAD using simple and low energy consumption devices and technique, in contrast to prior Vitamin E separation systems and techniques. Representative embodiments of the disclosure that are directed toward the extraction of Vitamin E in a manner that addresses one or more problems or limitations associated with prior Vitamin E extraction systems and techniques are detailed below with reference to FIGS. 1-2.

For purposes of brevity and clarity, aspects of various embodiments of the disclosure are described herein in the context of particular configurations suitable for Vitamin E extraction from FAD. This, however, does not preclude the applicability of aspects of the disclosure to other systems, subsystems, devices, and/or processes, where certain principles in accordance with the disclosure, such as structural, operational, functional or performance characteristics, are desired.

Representative Vitamin E Extraction Processes

A process for extracting Vitamin E from a plant-based source of Vitamin E such as a FAD in accordance with various embodiments of the disclosure generally includes multiple procedural steps. The process can include preparing a mixture of a FAD that includes Vitamin E and a non-polar solvent; reducing the temperature of the mixture sequentially to a series of pre-determined temperatures; removing solid fractions from the mixture when the temperature of the mixture reaches each of the pre-determined temperatures; and removing the non-polar solvent from the mixture for recovering Vitamin E from the mixture.

Figure 1:
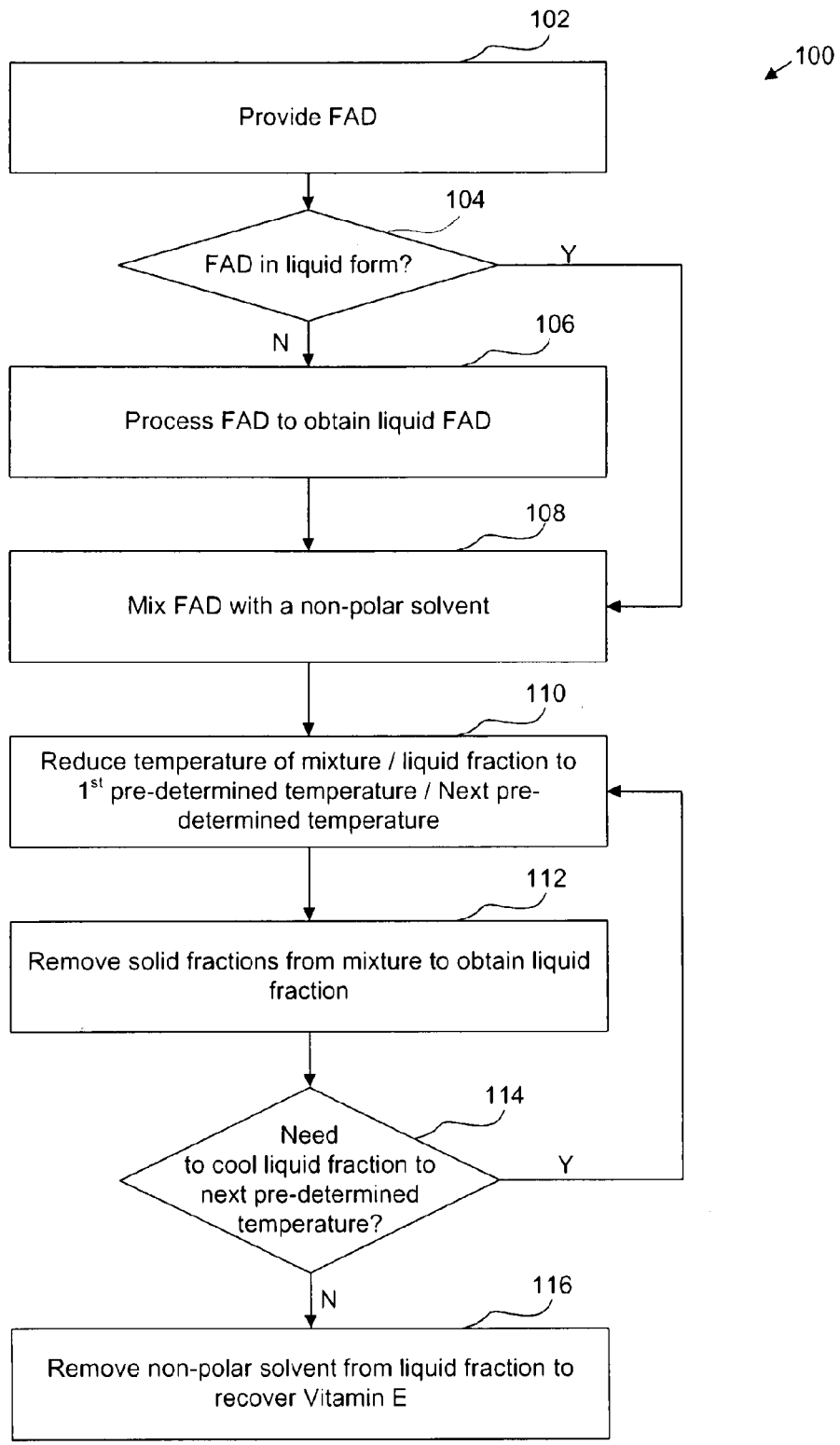
FIG. 1 is a flow chart of a Vitamin E extraction process according to an embodiment of the present disclosure.

FIG. 1 is a flow chart of a Vitamin E extraction process 100 according to an embodiment of the present disclosure. A first process portion 102 of the process 100 involves providing a FAD to an extraction system. Representative examples of a FAD that includes Vitamin E include one or more oil distillates, such as palm oil or rice oil. Embodiments of the disclosure are also suitable for extracting Vitamin E from a corresponding, analogous, or generally analogous type of natural oil such as a vegetable oil or the like. In a representative embodiment, the FAD can be a fatty acid distillate of palm oil.

Depending on embodiment details, the FAD can be provided in a liquid or solid form. A second process portion 104 can involve determining whether the FAD is in a liquid state. Generally, the FAD should be processed to obtain a liquid form before it can be mixed with a non-polar solvent. Hence, if the FAD is not provided in a liquid state, a third process portion 106 can involve processing the FAD to obtain a liquid preparation. For instance, in embodiments where the FAD is a solid, the FAD can be melted before it is further processed for Vitamin E extraction. In some embodiments, the FAD can be melted using an indirect heating method, which facilitates the prevention of FAD burning.

Indirect heating of the FAD can be performed, for example, via a heated bath. A solid FAD can be transferred or placed in a suitable container (e.g., a test-tube, flask, or other vessel), which is subsequently immersed into a heated bath (e.g. a heated water bath). The temperature of the heated bath can be controlled between approximately 30° C. and 100° C. so as to melt the FAD within the container. In various embodiments, the container carrying the FAD can be immersed into a heated bath having a temperature of approximately 60° C. The temperature of the heated bath can be subsequently increased to approximately 75° C. for melting the FAD. In a representative embodiment, the FAD in the container can be substantially or completely melted to a liquid state when the temperature of the heated bath is approximately 72° C.

A fourth process portion 108 involves mixing the liquid state FAD with a non-polar solvent. The non-polar solvent acts as a medium for dissolving the FAD. Particularly, the non-polar solvent has to have a sufficiently low electric polarity such that the Vitamin E present in the FAD can be effectively dissolved by the non-polar solvent. In several embodiments, the dielectric constant of the non-polar solvent can be between about 0.5 to 40.0. In a representative embodiment, the dielectric constant of the non-polar solvent can be approximately 2.0. In addition, it is desirable for the non-polar solvent to possess a high evaporation rate. A high evaporation rate ensures that the non-polar solvent can be easily and substantially removed for recovering Vitamin E at later stages of the process 100. In some embodiments, the non-polar solvent can carry or exhibit a low residue content of about 0.001% to about 2.0% after evaporation. In a representative embodiment, the non-polar solvent can have a residue content of about 0.001% after evaporation. Representative examples of a suitable non-polar solvent for this process include one or more of hexane, methanol, ethanol, n-propanol and the like. In a representative implementation, the non-polar solvent can be hexane.

In various embodiments, the FAD and non-polar solvent can be mixed at a FAD/non-polar solvent concentration ratio of at least 1:1. In some embodiments, the concentration ratio of FAD/non-polar solvent can be one of about 1:2, 1:3 or 1:4. In particular embodiments, the concentration of FAD can be approximately 50 g/mL and the concentration of hexane can be at least approximately 50 g/mL (e.g., about 100 g/mL, 150 g/mL or 200 g/mL). The FAD can be added to the non-polar solvent at approximately room temperature or a temperature generally proximate to room temperature (e.g. about 28° C. to 30° C.), followed by mixing, agitating or stirring of the mixture. In some embodiments, the mixture can be stirred at a speed of at least approximately 300 revolutions per minute (rpm). In a representative embodiment, the mixture can be stirred at a speed of about 350 to about 450 rpm.

A fifth process portion 110 can involve reducing the temperature of the mixture to a first pre-determined temperature. Stirring of the mixture of FAD and the non-polar solvent can be terminated once the temperature of the mixture reaches the first pre-determined temperature. As the temperature of the mixture approaches the first pre-determined temperature, components within the mixture having a freezing point higher or equivalent to the first pre-determined temperature will begin to solidify and form solid fractions or crystals within the mixture. On the other hand, components in the mixture having a freezing point lower than the first pre-determined temperature will remain as a liquid fraction.

Selection of the first pre-determined temperature is mainly dependent on the composition and the freezing point of the components within the FAD. For instance, the first pre-determined temperature can be selected such that when the temperature of the mixture approaches the first pre-determined temperature, a non-Vitamin E component of the mixture can solidify while the Vitamin E and the non-polar solvent remain in the liquid state. Additionally, when the solid fractions are formed, they can be interspersed among the liquid fraction within the mixture. Hence, the first pre-determined temperature should be selected such that the quantity of components having a freezing point higher than the first pre-determined temperature is insufficient for creating masses of solid fractions that will restrict the fluidity of the liquid fraction of the mixture. For instance, if an FAD, which is made up of a large proportion (e.g. 80%) of components having a freezing point higher than 10° C., is cooled directly from room temperature (e.g. about 28° C.) to a first pre-determined temperature of approximately 10° C., a solid clump will be obtained instead of a mixture of solid fractions and a free-flowing liquid fraction. In the absence of a mixture of solid fractions and a fluid liquid fraction, the component containing Vitamin E (i.e. the liquid fraction) cannot be separated from the non-Vitamin E components (i.e. the solid fraction) by a sixth process portion 112 and be recovered by the process 100, as further detailed below.

In a representative embodiment, where the FAD contains approximately 45% of palmitic acid and approximately 40% of oleic acid, the first pre-determined temperature can be approximately 20° C. As palmitic acid has a freezing point of about 63-64° C., the palmitic acid will form solid fractions at approximately 20° C. since its freezing point is higher than the first pre-determined temperature. On the other hand, since oleic acid has a freezing point of about 13-14° C., which is lower than the first pre-determined temperature, oleic acid remains in the liquid fraction. Hence, by selecting a suitable temperature (e.g., about 20° C.) as the first pre-determined temperature, bulk solidification of the mixture can be prevented. Typically, to obtain a reasonable yield of Vitamin E, the first pre-determined temperature can be any temperature between approximately 15° C. and 25° C. In a representative embodiment, the first pre-determined temperature can be approximately 20° C.

The sixth process portion 112 involves removing the solid fractions from the mixture. In various embodiments, the solid fractions can be separated from the mixture via conventional filtration techniques such as vacuum filtration, gravitational filtration and/or the like. In representative embodiments, separation of solid fractions from the mixture can be carried out using vacuum filtration with cellulose paper acting as a filter. The solid fractions can be collected on the filter (i.e., as residues) while the liquid fraction can penetrate the filter and be collected for subsequent process portions. In embodiments where energy consumption and processing time are of less importance, the solid fractions can also be separated from the mixture by conventional centrifugation techniques.

After separation of the solid fractions from the liquid fraction in the sixth process portion 112, a seventh process portion 114 can involve determining whether the liquid fraction collected from the sixth process portion 112 should be cooled to a next pre-determined temperature. If the liquid fraction should be cooled to a next pre-determined temperature, the process 100 returns to the fifth process portion 110 for a further reduction of the temperature of the liquid fraction to the next pre-determined temperature. If the liquid fraction need not be cooled to a next pre-determined temperature, the process 100 can proceed to an eighth process portion 116, as described in detail later.

Typically, after the first round of the sixth process portion 112, there can still be some non-Vitamin E components remaining in the liquid fraction. To facilitate the removal of the remaining non-Vitamin E portions, the liquid fraction can be further subjected to a number of cooling and separation cycles or stages (i.e., repetitions of the fifth and sixth process portions) over a series of pre-determined temperatures. Particularly, the liquid fraction can be cooled to a next pre-determined temperature (e.g., a second pre-determined temperature) of the series of pre-determined temperatures (i.e., the fifth process portion 110) followed by the separation of the solid fractions from the liquid fraction while maintaining the mixture at that pre-determined temperature. The solid fractions removed at the end of each cooling cycle (e.g., at the second pre-determined temperature) can include non-Vitamin E components that have solidified as they have a freezing point that is lower than the preceding pre-determined temperature (e.g., first pre-determined temperature) within the temperature series but higher than the following or subsequent pre-determined temperature (e.g., third pre-determined temperature) within the temperature series. Hence, multiple repetitions of the fifth and sixth process portions over a series of pre-determined temperatures aids in the sequential removal of non-Vitamin E components from the liquid fraction to obtain a liquid fraction which contains substantially or predominantly Vitamin E and the non-polar solvent.

Depending on embodiment details, the range of the series of the pre-determined temperature is selected to cover at least a broadest range of the freezing points of a set of non-Vitamin E components that are present in the mixture. This allows non-Vitamin E components present in the mixture to be solidified and removed through the multiple stages of cooling and separation process, to create a substantially pure concentration of Vitamin E and non polar solvent solution. For instance, in an embodiment where the FAD is suspected or known to include fatty acids such as palmitic acid (freezing point of about 63 to 64° C.), oleic acid (freezing point of about 13 to 14° C.) and linoleic acid (freezing point of about −11 to −12° C.), the liquid fraction can be cooled to a series of pre-determined temperatures between approximately 25° C. and −25° C. In some embodiments, the mixture is further cooled to a series of pre-determined temperatures between approximately 23° C. and −20° C. In a representative embodiment, the mixture is cooled to a series of pre-determined temperatures between approximately 20° C. and −15° C. In embodiments where energy consumption and process duration are of less significance, the cooling and separation cycles can be carried out over a span of pre-determined temperatures that is broader than 25° C. to −25° C.

In various embodiments, the series of the pre-determined temperatures can include or be a plurality of pre-determined temperature offsets defined relative to a reference temperature (e.g. a first pre-determined temperature). The series of pre-determined temperatures can contain at least two distinct pre-determined temperatures. In some embodiments, the mixture can be subjected to a cooling staircase of at least six distinct pre-determined temperatures. The multiple-stages cooling and separation process allows non-Vitamin E components to form solid fractions sequentially at the various cooling and separating stages based on their freezing points and the pre-determined temperature of the respective cooling and separation stages. This allows solid fractions that are formed during each cooling stage to be removed periodically from the liquid fraction. Periodic clearing of the solid fractions at the end of each cooling stages effectively avoids significant accumulation of solid fractions and bulk solidification of the mixture, thereby facilitating or allowing the separation of Vitamin E from the non-Vitamin E components of FAD. In some embodiments, the temperature of the liquid fraction can be reduced by 5° C. sequentially. Particularly, the liquid fraction can be cooled to a series of pre-determined temperatures including 15° C., 10° C., 5° C., 0° C., −5° C., −10° C., −15° C., with the first pre-determined temperature being 20° C.

Additionally, the yield of Vitamin E is dependent on the rate of cooling of the mixture over the series of pre-determined temperatures. The cooling rate is usually selected to provide sufficient time for the solidification of non-Vitamin E components of FAD at each of the cooling stages without causing any or any significant solidification of Vitamin E and the non-polar solvent. Furthermore, the pre-determined rate can be established or adjusted based on the target or intended processing time of the extraction process. Typically, the pre-determined rate can be about 0.5-5.0° C. per minute. In a representative embodiment, the pre-determined rate can be at least about 1° C. per minute. Hence, for a mixture to be cooled from 20° C. to −15° C., the cooling and extraction cycles of the extraction process can take slightly more than approximately 35 minutes.

The solid fractions removed from multiple stages of cooling and separating processes generally include free fatty acids such as palmitic acid, oleic acid, linoleic acid and the like. The solid fractions collected throughout the extraction process can be processed by various recovery and/or purification techniques such as fractional distillation to obtain useful compounds. These compounds may be used as raw materials in a wide variety of industries. For example, the free fatty acids extracted from the solid fraction can be used in the production of biodiesel. Palmitic acid can be used in the manufacture of pharmaceuticals, cosmetics, lube oils and food additives; oleic acid can be used in the manufacture of synthetic dairy products, while linoleic acid can be used in the manufacture of animal feeds, nutrient supplements, additives and medicine.

After completion of multiple stages of a cooling and separating process, the process 100 can proceed to an eighth process portion 116. The eighth process portion 116 involves removal of the non-polar solvent from the liquid fraction to recover Vitamin E. In various embodiments, the non-polar solvent can be removed by evaporation. In a representative embodiment, the non-polar solvent can be removed from the liquid fraction through evaporation under reduced pressure. As the boiling point of the non-polar solvent is dependent on the ambient pressure, the application of a reduced pressure to the liquid fraction will result in the reduction of the boiling point of the non-polar solvent, for example, from 68.7° C. under normal atmospheric pressure to a temperature that is lower than 68.7° C. Hence, evaporation of the non-polar solvent under reduced pressure eliminates the need to conduct evaporation under high temperature conditions, thereby resulting in lower energy consumption, improved process efficiency, and a reduced likelihood of Vitamin E degradation due to unnecessary heating. Depending upon embodiment details, the liquid fraction can be subjected to evaporation under a reduced pressure whereby the boiling point of the non-polar solvent can be controlled at a temperature that is slightly above room temperature. In an embodiment where hexane is used as the non-polar solvent, the non-polar solvent can be evaporated at a reduced pressure of approximately 290 mmHg. Under such reduced pressure, the boiling point of hexane is reduced from 68.7° C. to about 40° C.

Hence, it will be understood that the various parameters of the present disclosure such as one or more of the temperature range of and/or the temperatures within the series of pre-determined temperatures, cooling pattern, cooling rate, and temperature and pressure conditions for evaporating the non-polar solvent are important factors for controlling the efficiency of the extraction process as well as the quantity and quality of the Vitamin E yield. Accordingly, the parameters in the various embodiments of the present disclosure can be controlled, adjusted, or varied so that the process 100 can produce (1) maximal Vitamin E yield, using (2) an acceptable processing time, with (3) minimal energy consumption. Accordingly, the process 100 can be more cost-effective and efficient than other techniques for Vitamin E extraction that utilize undesirably complicated and time consuming laboratory techniques and methods.

Additionally, it will be understood that the Vitamin E extracted from various embodiments of the present disclosure can be further processed using existing Vitamin E extraction techniques to further enhance the quality, purity, and/or yield of the extracted Vitamin E. Examples of existing techniques that can be used to further process Vitamin E yield obtained with the techniques of the present disclosure includes any one of or a combination of saponification, transesterification, distillation, partitioning, crystallization, supercritical fluid extraction and column chromatography. In a representative embodiment, the Vitamin E extracted from various embodiments of the present disclosure can be further purified using a supercritical fluid extraction technique. This allows the production of a higher concentration of pure Vitamin E at a relatively lower cost in comparison to a production process which only utilizes the supercritical fluid extraction technique.

Representative System Structure and Operation

Figure 2:
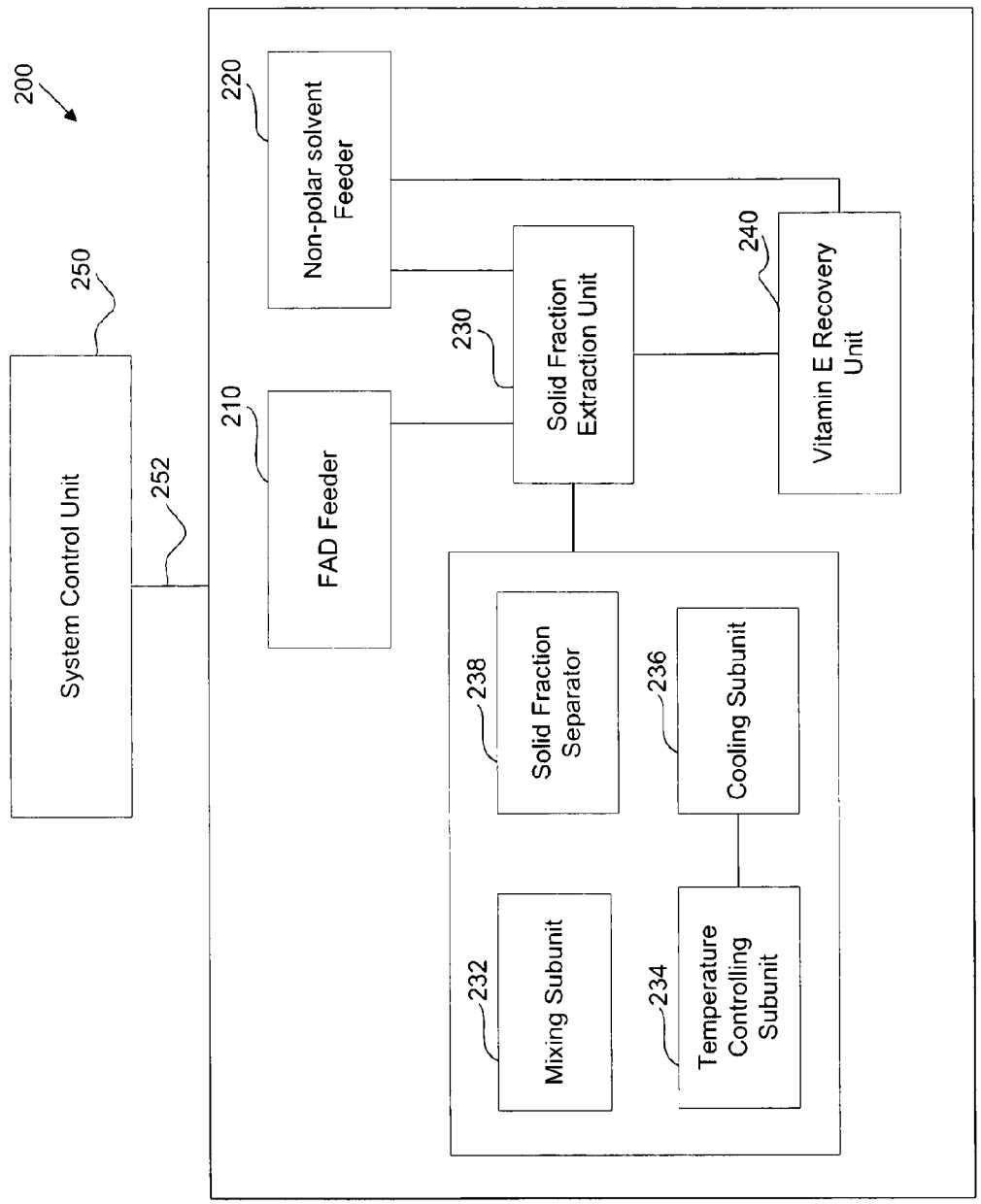
FIG. 2 shows a schematic diagram of a Vitamin E extraction system according to an embodiment of the present disclosure.

FIG. 2 is a block diagram of a representative extraction system 200 according to an embodiment of the disclosure. In an embodiment, the system 200 includes a FAD feeder 210, a non-polar solvent feeder 220, a solid fraction extraction unit 230 and a Vitamin E recovery unit 240. The extraction system 200 can additionally include a system control unit (SCU) 250, which can be configured to manage or direct one or more Vitamin E extraction operations or process portions. The SCU 250 can be coupled to particular Vitamin E subsystems, elements or devices by a link 252. The link 252 can facilitate, for instance, SCU 250 communication with one or more of the FAD feeder 210, non-polar solvent feeder 220, solid fraction extraction unit 230, and Vitamin E recovery unit 240, as further detailed below.

Particular elements of the Vitamin E extraction system 200 are structured in a manner that enables or facilitates the extraction of Vitamin E from a FAD based upon a multiple-stage, sequential cooling and separation process. For instance, a FAD feeder 210 can be structured, shaped, and/or machined for carrying, holding, or receiving a quantity of FAD in particular location, position and/or orientation for melting the FAD to a liquid state. The FAD feeder 210 can also be structured for directing, transferring, or feeding the FAD into the solid fraction extraction unit 230. The non-polar solvent feeder 220 can be structured, shaped, and/or machined for (1) receiving, carrying or holding a volume of non-polar solvent; (2) processing and cooling the temperature of non-polar solvent to a low temperature (e.g., room temperature); and (3) feeding the non-polar solvent to the solid fraction extraction unit 230. The solid fraction extraction unit 230 can be structured and configured for mixing the FAD with the non-polar solvent. Additionally, the solid fraction extraction unit 230 can be configured for cooling the mixture in a series of pre-determined temperatures, and removing solid fractions from the mixture at each of the pre-determined temperatures within the series of pre-determined temperatures. The solid fraction extraction unit 230 can be structured to provide, transfer, or output a liquid fraction, which includes substantially Vitamin E and the non-polar solvent, to the Vitamin E recovery unit 240. The Vitamin E recovery unit 240 can be structured and configured for separating the non-polar solvent from the Vitamin E, thereby recovering a Vitamin E extract for collection. Aspects of various embodiments of the disclosure can also include a Vitamin E recovery unit 240 that is configured for collecting and channeling a quantity of separated non-polar solvent to the non-polar solvent feeder 220 for reuse in subsequent Vitamin E extraction processes.

In various embodiments, the FAD feeder 210 includes a FAD receiving chamber for carrying, holding or receiving a quantity of FAD. Depending on the state of the FAD fed to the FAD feeder 210, the FAD feeder 210 can process and prepare the FAD into a liquid form for subsequent Vitamin E extraction procedures. To process the FAD into a liquid form, the FAD feeder 210 can include a melting unit in some embodiments. The melting unit can be, for instance, any device, apparatus or system that provides an indirect source for heating the FAD receiving chamber. For instance, the melting unit can be a heated water bath surrounding the FAD receiving chamber. The FAD feeder 210 can additionally include a FAD outlet for channeling and directing the liquid FAD to the solid fraction extraction unit 230. The FAD feeder 210 can additionally include or be coupled to one or more of a temperature sensor, a processing unit, a microcontroller, communication and/or control circuitry, and a memory.

The non-polar feeder 220 includes a non-polar solvent receiving unit for carrying, holding or receiving a quantity of non-polar solvent. The non-polar solvent receiving unit can receive non-polar solvent input from an external source or from the Vitamin E recovery unit 240, as further detailed below. The non-polar solvent feeder 220 can additionally include a temperature sensor and a cooling system. Depending on the temperature of the non-polar solvent carried by the non-polar solvent feeder 220, the cooling system can be configured or adjusted to cool the non-polar solvent to approximately room temperature before it is used for a subsequent Vitamin E extraction process. The non-polar solvent feeder 220 can also include a non-polar solvent outlet for channeling and directing the non-polar solvent to the solid fraction extraction unit 230. Additionally, the non-polar solvent cooling unit 220 can include or be coupled to one or more of a processing unit, a microcontroller, communication and/or control circuitry, and a memory.

The solid fraction extraction unit 230 includes several separate subunits. In some embodiments, the solid fraction extraction unit 230 can be a reactor vessel having a mixing subunit 232, a temperature controlling subunit 234, a cooling subunit 236 and a solid fraction separator 238. Each subunit of the solid fraction extraction unit 230 can be in communication with one or more of a processing unit, a microcontroller, communication and/or control circuitry, and a memory.

The mixing subunit 232 can receive liquid FAD from the FAD feeder 210 and the non-polar solvent from the non-polar solvent feeder 220. In several embodiments, the mixing subunit 232 can be equipped with or coupled to a device or apparatus for mixing the contents of the mixing chamber 232 (e.g., sonically and/or mechanically). In a representative embodiment, the mixing subunit 232 can be coupled to a mixing blade, a stirrer, an agitator or an ultrasonic transducer.

The solid fraction extraction unit 230 can include a temperature controlling subunit 234. The temperature controlling subunit 234 measures, monitors, and/or adjusts the temperature of the mixture of FAD and the non-polar solvent carried within the mixing subunit 232. The temperature controlling subunit 234 can include any of a temperature measuring device such as thermometer, temperature sensor, thermistor and the like. In various embodiments, the temperature controlling subunit 234 can include a cooling subunit 236 or be configured, structured or arranged so as to transmit, convey or communicate the measured temperature to a cooling subunit 236 or the system control unit 250.

The cooling subunit 236 can be actuated to control the temperature of the mixture within the mixing subunit 232. In several embodiments, the cooling subunit 236, in association with the temperature controlling subunit 234, can monitor the temperature of the mixture within the mixing subunit 232 and cool the temperature of the mixture sequentially to a series of pre-determined temperatures at a pre-determined rate. Additionally, as the temperature of the mixture reaches each of the pre-determined temperatures within the series of pre-determined temperatures, the cooling system can be configured, structured, arranged or directed to maintain the temperature of the mixture at the pre-determined temperature for a given amount of time so that any solid fractions formed at that cooling stage can be removed by a solid fraction separator 238. In several embodiments, the cooling subunit 236 can be a heat exchanger.

The solid fraction separator 238 can be a filtration or centrifugation device or apparatus. In some embodiments, the solid fraction extraction unit 230 can include a filter funnel which can receive the mixture from the mixing subunit 232. The filter funnel can be fitted with a cellulose filter paper. Due to the porosity of the cellulose filter paper, most of the solid fractions within the mixture can be prevented from penetrating the filter paper while the liquid fraction of the mixture passes through the filter paper. The filter funnel can be coupled to a filtrate collection tank. Hence, any liquid fraction that penetrates the filter paper of the filtrate collection tank can be collected in the filtrate collection tank. Additionally, the filtrate collection tank can be coupled to a vacuum pump. The vacuum pump can be actuated to create a state of vacuum within the filtrate collection tank, thereby creating a pressure gradient between the interior and exterior of the filtrate collection tank. This difference in pressure provides a suction force which urges the flow of the mixture from the filter funnel through the filter paper and into the filtrate collection tank.

The filtrate collection tank can be connected or coupled with the mixing subunit 232 so that the filtrate collected in the filtrate collection tank at the end of each separation process can be rechanneled to the mixing subunit 232 for subsequent cooling and separation cycles. In some embodiments, the filtrate collection tank can be coupled to a mechanical pump which can be actuated to force the filtrate collected within the filtration collection tank to flow back into the mixing subunit 232 after the completion of a separation process. In alternate embodiments, the filtrate collected within the filtration collection tank can be manually returned into the mixing subunit 232 after the completion of a separation process. Additionally, the filtrate collection tank can include outlets or channeling apparatuses for connecting or coupling the filtrate collection tank to the Vitamin E recovery unit 240. Such connection or coupling mechanisms allow the flow of liquid fraction, which is collected upon the completion of multiple stages of cooling and separation over the entire series of pre-determined temperatures, to the Vitamin E recovery unit 240 for processing.

To extract a suitable or substantial quantity of non-Vitamin E components from the mixture, the liquid fraction obtained from the solid fraction separator 238 should undergo several stages of cooling and separation. To carry out multiple stages of cooling and separation process within the solid fraction extraction unit 230, the various subunits within the solid fraction extraction unit 230 cooperatively interact during inter-subunit operations. For instance, after the solid fraction separator 238 has completed the first round of separation at the first pre-determined temperature, the liquid fraction collected in the filtration collection tank can be rechanneled back to the mixing subunit 232. The temperature controlling subunit 234 will then monitor the temperature of the liquid fraction that has been rechanneled back to the mixing subunit 232. Based on the temperature of the liquid fraction, the temperature controlling subunit 234 can convey or communicate the information relating to the cooling parameters to the cooling subunit 236 so that the cooling subunit 235 can act to decrease the temperature of the liquid in the mixing subunit 232 to the next pre-determined temperature within the series of the pre-determined temperatures. Once the temperature controlling subunit 234 senses that the temperature of the liquid fraction has reached the next pre-determined temperature of the series, the temperature controlling subunit 234 will terminate or interrupt the cooling effect of the cooling subunit 236. In conjunction, the temperature controlling subunit 234 will also trigger or activate the release of the mixture from the mixing subunit 232 into the solid fraction separator 238. These interactions between the subunits can repeat and continue until the all stages of cooling and separation of solid fractions have been completed over the series of pre-determined temperatures.

The Vitamin E recovery unit 240 can include a non-polar solvent removal unit. The non-polar solvent can be separated from the Vitamin E present in the liquid fraction by techniques such as evaporation and the like. In a representative embodiment, the non-polar solvent removal unit can include an apparatus (e.g., a vacuum pump) to facilitate evaporating the non-polar solvent under reduced pressure. In some embodiments, the apparatus can include a heating source for heating the liquid fraction to obtain non-polar solvent vapour; a condenser for cooling the non-polar solvent vapour; and a non-polar solvent tank for collecting the condensed non-polar solvent. The non-polar solvent tank can additionally be coupled to the non-polar solvent feeder 220 such that the non-polar solvent collected within the non-polar solvent tank can be channeled to the non-polar solvent feeder 220 for reuse in subsequent Vitamin E extraction processes.

In various embodiments, the SCU 250 can be a computer system (e.g., a desktop or laptop computer) or a computing device (e.g., an industrial control system) that is capable of receiving as inputs various parameters such as a weight and volume of FAD, a volume and concentration of the non-polar solvent, and a concentration ratio of the FAD to non-polar solvent to be fed to the solid fraction extraction unit 230. In some embodiments, process parameters such as the stirring speed, number of cooling and separation cycles, series of pre-determined temperatures, cooling rate and cooling pattern can also be input into the SCU 250. In alternate embodiments, the SCU 250 can be pre-installed with these instructions. The SCU 250 is capable of executing program instructions that are directed toward communicating with particular Vitamin E extraction system elements; and coordinating interaction and communication between various Vitamin E extraction system elements to extract Vitamin E extraction from an FAD in accordance with an embodiment of the disclosure.

Various embodiments of the system 200 include a set of communication links, lines or buses 252 that facilitate signal transfer between particular subsystems or devices of the system 200 with the SCU 250. Particular communication links 252 can facilitate, for instance, communication between the FAD feeder 210, the non-polar solvent feeder 220, the mixing subunit 232, the temperature controlling subunit 234, the cooling subunit 236 and the solid fraction separator 238 with the SCU 250.

In a representative embodiment, the system 200 can have a similar or analogous type of construction, and function, to a carotenoid extraction system as described in Thai Patent Publication No. 26260 (hereafter referred to as Thai Publication), which is herein incorporated by reference. For instance, the non-polar solvent feeder 220 can have a similar or analogous type of construction, and function to the set of apparatus for reducing temperature of hexane as described in Thai Publication, while the mixing subunit 232, temperature controlling subunit 234 and cooling subunit 236 may be analogous to the construction and function of the set of apparatus for mixing hexane and crude palm oil as described in the Thai Publication. Additionally, each of the solid fraction separator 238 and the Vitamin E recovery unit 240 has configurations, constructions and functions that are similar or analogous to the set of apparatus for separating fats crystal and the set of apparatuses for heat exchange, evaporating hexane, condensing hexane and collecting hexane of the system as described in the Thai Publication, correspondingly.

It will be understood in various embodiments of the present disclosure, the system 200 is energy and cost efficient, easy to implement, operate and maintained, and therefore is a suitable and affordable system for processing FAD to extract a reasonable yield of Vitamin E. Accordingly, the extraction process 100 implemented by the system 200 according to multiple embodiments of the present disclosure can be a versatile, convenient, fast, energy- and cost-efficient technique for extracting Vitamin E in comparison to conventional Vitamin E extraction techniques.

Although the above-disclosed structures, features and functions, processes and techniques, or alternatives thereof have been illustrated with reference to particular representative embodiments, it is not intended that other embodiments be limited to or in view of particular embodiments described herein. A number of modifications and variations can be made without departing from the spirit or scope of the disclosure. The above-disclosed structures, features and functions, processes and techniques, or alternatives thereof, as well as various presently unforeseen or unanticipated alternatives, modifications, variations or improvements thereto, are encompassed by the following claims.

The invention claimed is:

1. A method for recovering Vitamin E from fatty acid distillate (FAD), comprising:
    providing a mixture of the FAD and a non-polar solvent to extract at least a portion of the Vitamin E from the FAD into the non-polar solvent;
    reducing the temperature of the mixture sequentially in a series of cooling stages having temperatures between 25° C. to −25° C. based on the freezing temperatures of non-Vitamin E components and a cooling rate between 0.5° C.-5° C. per minute such that each cooling stage solidifies at least a portion of the FAD to form a solid fraction in the mixture without causing solidification of the Vitamin E;
    removing the solid fraction comprising fatty acids from the mixture when the temperature of the mixture reaches each of the cooling stages; and
    removing the non-polar solvent from the mixture for recovering Vitamin E,
    wherein the FAD is prepared into a liquid form prior to forming the mixture with the non-polar solvent.

2. The method of claim 1, wherein the FAD comprises palmitic acids and oleic acids.

3. The method of claim 2, wherein the temperature is reduced to 10° C. to −25° C. to solidify the oleic acids.

4. The method of claim 1, wherein reducing the temperature of the mixture is at a rate of at least 1° C. per minute.

5. The method of claim 1, wherein the reducing the temperature of the mixture is by 5° C. for each cooling stage.

6. The method of claim 1, wherein the non-polar solvent comprises at least one of hexane, methanol, ethanol and n-propanol.

7. The method of claim 1, further comprising providing the mixture of the FAD and the non-polar solvent FAD with a FAD: non-polar solvent concentration ratio of at least 1:1-4 by weight per volume.

8. The method of claim 1, wherein the fatty acid distillate (FAD) comprises a palm oil distillate.

9. The method of claim 1, wherein the FAD of liquid form is produced by heating the FAD of solid form in a water bath.

10. The method of claim 1, wherein removing the non-polar solvent from the mixture comprises evaporating the non-polar solvent.

11. The method of claim 1, further comprising purifying the recovered Vitamin E after removing the non-polar solvent from the mixture for recovering Vitamin E.

12. The method of claim 11, wherein purifying the recovered Vitamin E comprises subjecting the recovered Vitamin E to at least one of saponification, transesterification, distillation, solvent extraction, partitioning, crystallization, supercritical fluid extraction and column chromatography process.

13. A method of extracting Vitamin E from fatty acid distillate comprising bringing FAD into contact with a non-polar solvent to form a mixture and extracting at least portion of vitamin E into the non-polar solvent;

reducing temperature of the mixture to solidify the at least a portion of the FAD;

separating the solidified FAD from the mixture; and vaporizing the non-polar solvent from the mixture to acquire crude containing vitamin E, wherein the FAD comprises palmitic acids and oleic acids, wherein the temperature is reduced to 15° C. to −25° C. to solidify the palmitic acids.

14. The method of claim 13, wherein the FAD and non-polar solvent is in a ratio of 1:1-4 by weight per volume.

15. The method of claim 13, wherein the non-polar solvent is any one or combination of hexane, methanol, ethanol and n-propanol.

16. The method of claim 1, further comprising using a solid fraction removed from the mixture in the manufacture of one of biodiesel, pharmaceuticals, cosmetics, lube oils, food additives, synthetic dairy products, and animal feeds.

* * * * *